United States Patent [19]

Shuto et al.

[11] Patent Number: 5,405,989
[45] Date of Patent: Apr. 11, 1995

[54] PROPARGYL ESTER COMPOUNDS, ACARICIDES CONTAINING THE SAME AS AN ACTIVE INGREDIENT AND AN ACARICIDAL METHOD

[75] Inventors: Akira Shuto, Ashiya; Tohei Takagaki, Niihama; Hirosi Kisida, Takarazuka; Yoji Takada, Toyonaka; Takao Ishiwatari, Minoo, all of Japan

[73] Assignee: Sumitomo Chemical Co., Ltd., Osaka, Japan

[21] Appl. No.: 149,370

[22] Filed: Nov. 9, 1993

[30] Foreign Application Priority Data

Nov. 10, 1992 [JP] Japan .................... 4-299615

[51] Int. Cl.6 .................................. C07C 69/76
[52] U.S. Cl. .................................. 560/105; 560/55
[58] Field of Search ............ 560/105, 55; 514/532

[56] References Cited

U.S. PATENT DOCUMENTS

| | | | |
|---|---|---|---|
| 4,668,815 | 5/1987 | Enari et al. | 560/55 |
| 4,767,782 | 8/1988 | Seppelt et al. | |
| 5,066,675 | 11/1991 | Bühmann et al. | 514/544 |

FOREIGN PATENT DOCUMENTS

| | | |
|---|---|---|
| 0203607 | 3/1986 | European Pat. Off. |
| 0235722 | 9/1987 | European Pat. Off. |
| 3230775 | 2/1984 | Germany . |
| 559044 | 1/1980 | Japan . |
| 381202 | 4/1991 | Japan . |

*Primary Examiner*—Paul J. Killos
*Attorney, Agent, or Firm*—Cushman Darby & Cushman

[57] ABSTRACT

A propargyl ester compound of the formula (I),

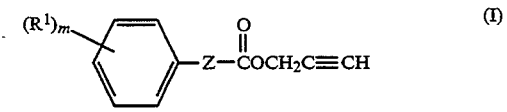

wherein $R^1$ is hydrogen, halogen, $C_1-C_4$ alkyl or $C_1-C_4$ alkoxy; Z is $C_5-C_{10}$ alkylene which may be substituted with $C_1-C_4$ alkyl; and m is an integer of from 1 to 5; with the proviso that when m is an integer of 2 or more, the substituents represented by $R^1$ may be the same or different; is incorporated into an acaricidal composition as an active ingredient, which can be used for controlling acarines.

8 Claims, No Drawings

PROPARGYL ESTER COMPOUNDS, ACARICIDES CONTAINING THE SAME AS AN ACTIVE INGREDIENT AND AN ACARICIDAL METHOD

The present invention relates to an acaricide, particularly an acaricide suitable for controlling house dust mites.

DE-A-3230775A1 discloses that a certain kind of propargyl ester compound can be used as an active ingredient for insecticides and spider mite-controlling agents. These compounds, however, may not always be satisfactory as an active ingredient for acaricides, particularly acaricides for house dust mites in terms of persistency and the like.

In view of such a situation, the present inventors have extensively studied to develop an excellent acaricide, and as a result have found that a propargyl ester compound of the formula (I),

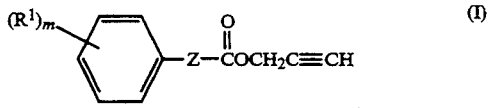

wherein $R^1$ is hydrogen, halogen, $C_1$-$C_4$ alkyl or $C_1$-$C_4$ alkoxy; Z is $C_5$-$C_{10}$ alkylene which may be substituted with $C_1$-$C_4$ alkyl; and m is an integer of from 1 to 5; with the proviso that when m is an integer of 2 or more, the substituents represented by $R^1$ may be the same or different; has an excellent acaricidal activity. The present inventors thus completed the present invention.

The present invention provides a propargyl ester compound of the formula (I) (hereinafter referred to as present compound), an acaricidal composition containing the compound as an active ingredient and a method for controlling acarines by applying the composition.

The present compound is excellent in immediate effect and persistency about acaricidal activity, and further it has no such offensive odor as would become a problem.

In the present compound, the $C_1$-$C_4$ alkyl group in $R^1$ and Z includes for example methyl, ethyl, n-propyl, isopropyl and n-butyl. The halogen atom in $R^1$ includes for example fluorine, chlorine and bromine. The $C_1$-$C_4$ alkoxy group in $R^x$ includes for example methoxy, ethoxy, n-propyloxy, isopropyloxy and n-butyloxy and the like.

Of the present compounds represented by the formula (I), preferred are compounds having a molecular weight of about 230 to about 300.

The present compound can be produced, for example, by the following methods. Method A:

A method including the step of reacting an acid halide compound of the formula (II),

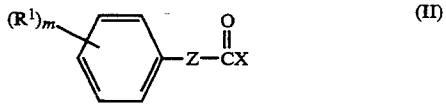

wherein $R^1$, Z and m are as defined above, and X is chlorine or bromine, with propargyl alcohol in the presence of a base.

This reaction is usually carried out in a solvent. The usable solvent includes ethers (e.g. diethyl ether, tetrahydrofuran and dioxane), aromatic hydrocarbons (e.g. toluene, benzene and xylene), hydrocarbons (e.g. n-hexane, n-heptane and cyclohexane), halogenated hydrocarbons (e.g. methylene chloride, chloroform, carbon tetrachloride, 1,2-dichloroethane and chlorobenzene), esters (e.g. ethyl acetate and methyl acetate), water, nitriles (e.g. acetonitrile), polar solvents (e.g. N,N-dimethylformamide, N,N-dimethylacetamide, N-methylpyrrolidone, dimethyl sulfoxide and pyridine) and the mixtures thereof.

When this reaction is carried out in a two-phase system using water as a solvent, the reaction can be accelerated by using a phase transfer catalyst such as tetra-n-butylammonium bromide, benzyltriethylammonium chloride and the like.

The usable base includes organic bases (e.g. pyridine, triethylamine), alkali hydroxides (e.g. sodium hydroxide and potassium hydroxide) and alkali carbonates (e.g. sodium carbonate and potassium carbonate).

The reaction temperature is usually within the range of from −20° C. to the boiling point of the solvent used, preferably from 0° C. to 50° C.

The molar ratio of the starting materials and base used for the reaction can be optionally determined. However, it is advantageous to carry out this reaction using the acid halide compound, propargyl alcohol and the base in an equimolar ratio or a ratio near equimolar ratio.

Method B

A method including the step of reacting a carboxylic acid compound of the formula (III),

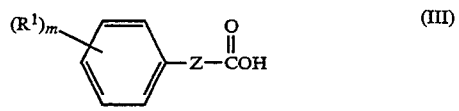

wherein $R^1$, Z and m are as defined above, with propargyl alcohol in the presence or absence of a dehydrating agent.

(a) When the dehydrating agent is not used, the reaction can be carried out without a solvent. In the case a solvent is used, the solvent includes polar solvents (e.g. N,N-dimethylformamide, N,N-dimethylacetamide, N-methylpyrrolidone and dimethyl sulfoxide), aromatic hydrocarbons (e.g. benzene, toluene and xylene), chlorobenzene and the like. The reaction temperature is usually within the range of from 50° C. to 250° C.

If necessary, acidic substances such as sulfuric acid, benzenesulfonic acid, p-toluenesulfonic acid, activated silica gel, etc. can be used as a catalyst for reaction in an amount of 0.0001 to 1 part by weight per part by weight of the carboxylic acid compound of the formula (III).

The molar ratio of the starting materials used for the reaction can be optionally determined, but it is advantageous to carry out this reaction at an equimolar ratio or a ratio near equimolar ratio.

(b) In the case a dehydrating agent is used in this reaction, the dehydrating agent includes for example carbodiimides (e.g. dicyclohexylcarbodiimide and 1-ethyl-3-(3-dimethylaminopropyl)carbodiimide), inorganic dehydrating agents (e.g. silicon tetrachloride) and the like. A solvent is not always necessary, but an inert organic solvent may be used. The inert organic solvent includes for example aliphatic hydrocarbons (e.g. n-pentane, n-hexane and n-heptane), aromatic hydrocarbons (e.g. benzene, toluene and xylene), chlorinated hydrocarbons (e.g. methylene chloride, chloroform, carbon tetrachloride, tetrachloroethylene, 1,2-dichloroethane, chlorobenzene and o-dichlorobenzene), esters (e.g. methyl acetate and ethyl acetate), amides (e.g. N,N-dimethylformamide, N,N-dimethylacetamide and N-methylpyrrolidone), nitriles (e.g. acetonitrile), ethers (e.g. diethyl ether, tetrahydrofuran and dioxane), pyridine, cyclohexane and the like.

The reaction temperature is usually within the range of from −20° C. to +100° C. The molar ratio of the starting materials and dehydrating agent used for the reaction can be optionally determined. However, it is advantageous to carry out this reaction using the carboxylic acid compound, propargyl alcohol and the dehydrating agent in an equimolar ratio or a ratio near equimolar ratio.

Method C

A method including the step of reacting the carboxylic acid compound of the foregoing formula (III) with a compound of the formula (IV),

wherein Y is halogen (e.g. chlorine, bromine), mesyloxy or tosyloxy, in the presence of a base.

The usable base includes alkali hydroxides (e.g. sodium hydroxide and potassium hydroxide), alkali carbonates (e.g. sodium carbonate and potassium carbonate), alkali metal hydrides (e.g. sodium hydride), organic bases (e.g. triethylamine) and the like.

The usable solvent includes ketones (e.g. acetone and methyl ethyl ketone), ethers (e.g. diethyl ether, tetrahydrofuran and dioxane), aromatic hydrocarbons (e.g. toluene, benzene, xylene and chlorobenzene), non-aromatic hydrocarbons (e.g. n-hexane, n-heptane and cyclohexane), esters (e.g. ethyl acetate and methyl acetate), nitriles (e.g. acetonitrile), polar solvents (e.g. N,N-dimethylformamide, N,N-dimethylacetamide, N-methylpyrrolidone and dimethyl sulfoxide), pyridine and the mixtures thereof.

The reaction temperature is usually within the range of from −20° C. to +100° C., preferably 0° C. to 50° C. The molar ratio of the starting materials and base used for the reaction can be optionally determined. However, it is desirable to carry out this reaction using the carboxylic acid compound, the compound of formula (IV) and the base in an equimolar ratio or a ratio near equimolar ratio.

In this reaction, the carboxylic acid compound of the formula (III) can be replaced by its alkali metal salt. In such a case, the presence of the base is not always necessary.

Method D

A method including the step of reacting an ester compound of the formula (V),

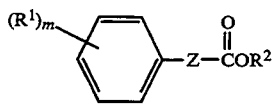

wherein $R^1$, Z and m are as defined above, and $R^2$ is $C_1$–$C_3$ alkyl (e.g. methyl, ethyl, n-propyl), with propargyl alcohol in the presence of a catalyst.

This reaction can be carried out without a solvent. In the case a solvent is used, the solvent includes ethers (e.g. diethyl ether, tetrahydrofuran and dioxane), aromatic hydrocarbons (e.g. toluene, benzene and xylene), aliphatic hydrocarbons (e.g. n-hexane, n-heptane and cyclohexane), halogenated hydrocarbons (e.g. methylene chloride, chloroform, carbon tetrachloride, 1,2-dichloroethane and chlorobenzene), and the like.

The usable catalyst includes acidic substances such as sulfuric acid, p-toluenesulfonic acid, benzenesulfonic acid and the like.

The reaction temperature is usually within the range of from 50° C. to either the boiling point of the solvent used or 200° C. The molar ratio of the starting materials used for the reaction can be optionally determined, but it is desirable to use propargyl alcohol in an amount of 2 moles or more per mole of the ester compound of the formula (V). The catalyst can be used in an amount of 0.0001 to 1 part by weight per part by weight of the ester compound.

After completion of the reaction, the desired present compound can be obtained by subjecting the reaction solution to the usual after-treatment such as extraction with an organic solvent, concentration and the like. If necessary, the resulting compound can be purified by the usual operations such as chromatography, distillation, recrystallization and the like.

Some of the thus obtained compounds contain an asymmetric carbon. The compound of the present invention includes each of the optically active isomers ((+)-and (−)-isomers) and the mixtures thereof in an optional ratio.

The acid halide compound of the formula (II) can be produced from the carboxylic acid compound of the formula (III) by the methods described in J. Amer. Chem. Soc., 67, 408 (1945), J. Chem. Soc., 79, 602 (1902) and the like.

Commercially available products may be used for the carboxylic acid compound of the formula (III). Alternatively, the carboxylic acid compound may be produced according to the method described in Nippon Kagaku Zasshi, Vol. 88, No. 6 (1967), etc., or the methods described in Org. Synth., I, 436 (1941) and Org. Synth. II, 474 (1943).

The ester compound of the formula (V) can be produced according to the methods described in Chem. Ber. 90, 1519 (1957), Liebigs Ann. Chem. 690, 79 (1965) and the like.

Some examples of the present compound are shown in Table 1, but the present compound should not be interpreted as being limited to these examples.

TABLE 1

| Compounds of the formula (I) | |
|---|---|
| $(R^1)_m$ | Z |
| H | $-(CH_2)_5-$ |
| H | $-(CH_2)_6-$ |
| H | $-(CH_2)_7-$ |
| H | $-(CH_2)_8-$ |
| H | $-(CH_2)_9-$ |

TABLE 1-continued

| $(R^1)_m$ | Z |
|---|---|
| H | $-(CH_2)_{10}-$ |
| 4-Cl | $-(CH_2)_4\underset{\underset{CH_3}{\|}}{CH}-$ |
| 4-Cl | $-(CH_2)_5\underset{\underset{CH_3}{\|}}{CH}-$ |
| H | $-(CH_2)_4\underset{\underset{CH_3}{\|}}{CH}-$ |
| H | $-(CH_2)_5\underset{\underset{CH_3}{\|}}{CH}-$ |
| H | $-(CH_2)_6\underset{\underset{CH_3}{\|}}{CH}-$ |
| H | $-(CH_2)_4\underset{\underset{C_2H_5}{\|}}{CH}-$ |
| H | $-(CH_2)_5\underset{\underset{C_2H_5}{\|}}{CH}-$ |
| H | $-(CH_2)_4\underset{\underset{n-C_3H_7}{\|}}{CH}-$ |
| H | $-(CH_2)_4\underset{\underset{i-C_3H_7}{\|}}{CH}-$ |
| H | $-(CH_2)_4\underset{\underset{n-C_4H_9}{\|}}{CH}-$ |
| H | $-(CH_2)_2\underset{\underset{CH_3}{\|}}{CH}-(CH_2)_2-$ |
| H | $-(CH_2)_3\underset{\underset{CH_3}{\|}}{CH}-CH_2-$ |
| H | $-CH_2-\underset{\underset{CH_3}{\|}}{CH}-(CH_2)_3-$ |
| H | $-\underset{\underset{CH_3}{\|}}{CH}-(CH_2)_4-$ |
| H | $-(CH_2)_4\underset{\underset{CH_3}{\|}}{CH}-CH_2-$ |
| H | $-(CH_2)_3\underset{\underset{CH_3}{\|}}{CH}-(CH_2)_2-$ |
| H | $-(CH_2)_2\underset{\underset{CH_3}{\|}}{CH}-(CH_2)_3-$ |
| H | $-CH_2-\underset{\underset{CH_3}{\|}}{CH}-(CH_2)_4-$ |
| H | $-\underset{\underset{CH_3}{\|}}{CH}-(CH_2)_5-$ |
| 4-Cl | $-(CH_2)_2\underset{\underset{CH_3}{\|}}{CH}-(CH_2)_2-$ |
| 4-Cl | $-\underset{\underset{CH_3}{\|}}{CH}-(CH_2)_4-$ |
| 4-Cl | $-\underset{\underset{C_2H_5}{\|}}{CH}-(CH_2)_4-$ |
| 4-Cl | $-(CH_2)_2\underset{\underset{C_2H_5}{\|}}{CH}-(CH_2)_2-$ |
| 4-Cl | $-(CH_2)_3\underset{\underset{C_2H_5}{\|}}{CH}-CH_2-$ |
| H | $-(CH_2)_2\underset{\underset{C_2H_5}{\|}}{CH}-(CH_2)_2-$ |
| H | $-(CH_2)_3\underset{\underset{C_2H_5}{\|}}{CH}-CH_2-$ |
| H | $-CH_2-\underset{\underset{C_2H_5}{\|}}{CH}-(CH_2)_3-$ |
| H | $-\underset{\underset{C_2H_5}{\|}}{CH}-(CH_2)_4-$ |
| 4-Cl | $-\underset{\underset{C_2H_5}{\|}}{CH}-(CH_2)_4-$ |
| H | $-(CH_2)_2\underset{\underset{C_2H_5}{\|}}{CH}-(CH_2)_3-$ |
| H | $-(CH_2)_5\underset{\underset{C_2H_5}{\|}}{CH}-$ |
| 4-CH$_3$ | $-(CH_2)_7-$ |
| 3-CH$_3$ | $-(CH_2)_7-$ |
| 2-CH$_3$ | $-(CH_2)_7-$ |
| 4-CH$_3$ | $-(CH_2)_5-$ |
| 3-CH$_3$ | $-(CH_2)_5-$ |
| 2-CH$_3$ | $-(CH_2)_5-$ |
| 4-CH$_3$ | $-(CH_2)_6-$ |
| 3-CH$_3$ | $-(CH_2)_6-$ |
| 2-CH$_3$ | $-(CH_2)_6-$ |
| 2,4-(CH$_3$)$_2$ | $-(CH_2)_5-$ |
| 4-i-C$_3$H$_7$ | $-(CH_2)_5-$ |
| 4-n-C$_4$H$_9$ | $-(CH_2)_5-$ |

TABLE 1-continued

Compounds of the formula (I)

| $(R^1)_m$ | Z |
|---|---|
| 4-$C_2H_5$ | $+CH_2\!\!\)_{\overline{5}}$ |
| 2,4,6-$(CH_3)_3$ | $+CH_2\!\!\)_{\overline{5}}$ |
| 4-F | $+CH_2\!\!\)_{\overline{5}}$ |
| 2-Cl | $+CH_2\!\!\)_{\overline{5}}$ |
| 3-Cl | $+CH_2\!\!\)_{\overline{5}}$ |
| 2,3-$Cl_2$ | $+CH_2\!\!\)_{\overline{5}}$ |
| 3,4-$Cl_2$ | $+CH_2\!\!\)_{\overline{5}}$ |
| 2,6-$Cl_2$ | $+CH_2\!\!\)_{\overline{5}}$ |
| 3,5-$Cl_2$ | $+CH_2\!\!\)_{\overline{5}}$ |
| 2-$OCH_3$ | $+CH_2\!\!\)_{\overline{5}}$ |
| 3-$OCH_3$ | $+CH_2\!\!\)_{\overline{5}}$ |
| 4-$OCH_3$ | $+CH_2\!\!\)_{\overline{5}}$ |
| 4-$OC_2H_5$ | $+CH_2\!\!\)_{\overline{5}}$ |
| 3-$OC_2H_5$ | $+CH_2\!\!\)_{\overline{5}}$ |
| 2,3-$(CH_3)_2$, 4-$OCH_3$ | $+CH_2\!\!\)_{\overline{5}}$ |
| 3-$CH_3$, 4-$OCH_3$ | $+CH_2\!\!\)_{\overline{5}}$ |
| 2,3,5-$Cl_3$ | $+CH_2\!\!\)_{\overline{5}}$ |
| 2,3,6-$Cl_3$ | $+CH_2\!\!\)_{\overline{5}}$ |
| 2,3,4-$Cl_3$ | $+CH_2\!\!\)_{\overline{5}}$ |
| 4-n-$C_3H_7$ | $+CH_2\!\!\)_{\overline{5}}$ |
| 4-Cl | $+CH_2\!\!\)_{\overline{5}}$ |
| 3,4-$Cl_2$ | $+CH_2\!\!\)_{\overline{5}}$ |
| 4-Cl | $+CH_2\!\!\)_{\overline{6}}$ |
| 3-Cl | $+CH_2\!\!\)_{\overline{6}}$ |
| 2-Cl | $+CH_2\!\!\)_{\overline{6}}$ |
| 3,4-$Cl_2$ | $+CH_2\!\!\)_{\overline{6}}$ |
| 4-Cl | $+CH_2\!\!\)_{\overline{7}}$ |
| 3-Cl | $+CH_2\!\!\)_{\overline{8}}$ |
| 4-Cl | $+CH_2\!\!\)_{\overline{9}}$ |
| 4-Cl | $+CH_2\!\!\)_{\overline{10}}$ |
| 4-F | $+CH_2\!\!\)_{\overline{7}}$ |
| 4-F | $+CH_2\!\!\)_{\overline{8}}$ |
| 4-F | $+CH_2\!\!\)_{\overline{9}}$ |
| 4-F | $+CH_2\!\!\)_{\overline{10}}$ |
| 3,4-$F_2$ | $+CH_2\!\!\)_{\overline{5}}$ |
| 3,4-$F_2$ | $+CH_2\!\!\)_{\overline{10}}$ |
| 4-$CH_3$ | $+CH_2\!\!\)_{\overline{8}}$ |
| 4-$CH_3$ | $+CH_2\!\!\)_{\overline{7}}$ |
| 4-$CH_3$ | $+CH_2\!\!\)_{\overline{4}}CH(CH_3)-$ |
| 4-$CH_3$ | $+CH_2\!\!\)_{\overline{4}}CH(C_2H_5)-$ |
| 4-F | $+CH_2\!\!\)_{\overline{4}}CH(CH_3)-$ |
| 4-$CH_3$ | $+CH_2\!\!\)_{\overline{5}}CH(CH_3)-$ |
| 4-$CH_3$ | $+CH_2\!\!\)_{\overline{4}}CH(C_2H_5)-$ |
| 4-$CH_3$ | $+CH_2\!\!\)_{\overline{2}}CH(CH_3)+CH_2\!\!\)_{\overline{2}}$ |
| 4-$CH_3$ | $+CH_2\!\!\)_{\overline{3}}CH(CH_3)-CH_2-$ |
| 4-$CH_3$ | $-CH_2-CH(CH_3)+CH_2\!\!\)_{\overline{3}}$ |
| 4-$CH_3$ | $-CH(CH_3)+CH_2\!\!\)_{\overline{4}}$ |
| 4-$CH_3$ | $+CH_2\!\!\)_{\overline{4}}CH(CH_3)-CH_2-$ |
| 4-$CH_3$ | $+CH_2\!\!\)_{\overline{3}}CH(CH_3)+CH_2\!\!\)_{\overline{2}}$ |
| 4-$CH_3$ | $+CH_2\!\!\)_{\overline{2}}CH(CH_3)+CH_2\!\!\)_{\overline{3}}$ |
| 3-$CH_3$ | $-CH_2-CH(CH_3)+CH_2\!\!\)_{\overline{4}}$ |
| 3-$CH_3$ | $-CH(CH_3)+CH_2\!\!\)_{\overline{5}}$ |
| 4-$CH_3$ | $+CH_2\!\!\)_{\overline{2}}CH(CH_3)+CH_2\!\!\)_{\overline{4}}$ |
| 4-$CH_3$ | $+CH_2\!\!\)_{\overline{4}}CH(CH_3)+CH_2\!\!\)_{\overline{2}}$ |

TABLE 1-continued

Compounds of the formula (I)

| $(R^1)_m$ | Z |
|---|---|
| 4-F | $-CH(CH_3)(CH_2)_4-$ |
| 4-F | $-CH(C_2H_5)(CH_2)_4-$ |
| 4-CH$_3$ | $-(CH_2)_2CH(C_2H_5)(CH_2)_2-$ |
| 4-CH$_3$ | $-(CH_2)_3CH(C_2H_5)-CH_2-$ |
| 4-CH$_3$ | $-(CH_2)_2CH(C_2H_5)(CH_2)_2-$ |
| 4-CH$_3$ | $-(CH_2)_3CH(C_2H_5)-CH_2-$ |
| 4-CH$_3$ | $-CH_2-CH(C_2H_5)(CH_2)_3-$ |
| 4-CH$_3$ | $-CH(C_2H_5)(CH_2)_4-$ |
| 4-CH$_3$ | $-CH(C_2H_5)(CH_2)_5-$ |
| 4-CH$_3$ | $-(CH_2)_3CH(C_2H_5)(CH_2)_2-$ |
| 2,3-(OCH$_3$)$_2$ | $-(CH_2)_5-$ |
| 2,6-(OCH$_3$)$_2$ | $-(CH_2)_5-$ |
| 2-OC$_2$H$_5$, 3-OCH$_3$ | $-(CH_2)_5-$ |
| 2,3-(OC$_2$H$_5$)$_2$ | $-(CH_2)_5-$ |
| 3-F, 4-OCH$_3$ | $-(CH_2)_5-$ |
| 2,4-(OCH$_3$)$_2$ | $-(CH_2)_5-$ |
| 2,5-(OCH$_3$)$_2$ | $-(CH_2)_5-$ |
| 3,4-(OCH$_3$)$_2$ | $-(CH_2)_5-$ |
| 3-OC$_2$H$_5$, 4-OCH$_3$ | $-(CH_2)_5-$ |
| 3,5-(OCH$_3$)$_2$ | $-(CH_2)_5-$ |
| 2,5-(CH$_3$)$_2$, 4-OCH$_3$ | $-(CH_2)_5-$ |
| 2,3-(CH$_3$)$_2$, 4-OCH$_3$ | $-(CH_2)_5-$ |
| 4-Br | $-(CH_2)_5-$ |
| 4-Br | $-(CH_2)_6-$ |
| 2-Br | $-(CH_2)_5-$ |
| 3-Br | $-(CH_2)_5-$ |
| 2,4-Br$_2$ | $-(CH_2)_5-$ |
| 2-F, 4-Br | $-(CH_2)_5-$ |
| 2-Cl, 4-Br | $-(CH_2)_5-$ |
| 3-Br, 4-F | $-(CH_2)_5-$ |
| 2,4-F$_2$ | $-(CH_2)_5-$ |
| 2,5-F$_2$ | $-(CH_2)_5-$ |

Mites which can be controlled by the present compound include for example the following: House dust mites: Epidermoptidae represented by (*Dermatophagoides farinae* Hughes) and *Dermatophagoides pteronyssinus*; Acaridae represented by common grain mite (*Tyrophagus putrescentiae*) and brown legged grain mite (*Aleuroglyphus ovatus*); Glycyphagidae represented by *Glycyphagus privatus* Oudemans, furniture mite (*Glycyphagus domesticus*) and groceries mite (*Glycyphagus destructor*); Cheyletidae represented by *Cheyletus malaccensis* Oudemans and *Cheyletus fortis* Oudemans; Tarsonemidae; Chortoglyphus spp.; and Haplochthoniidae. Ticks and parasitic mites of domestic animals: Ixodidae such as *Boophilus microplus*, etc.; *Ornithonyssus bacoti* Hirst, fowl mite (*Ornithonyssus sylviarum* Canestrini et Fanzago, poultry mite (*Dermanyssus gallinae*), etc.

When the present compounds are used as an active ingredient for acaricides, they may be used as they are without adding any other ingredients. Usually, however, they are formulated into oil sprays, emulsifiable concentrates, wettable powders, flowable concentrates, dusts, aerosols, smoking formulations, foggings, poison baits, mite-controlling sheets and the like. In preparing these formulations, the present compounds are mixed with a solid carrier, a liquid carrier, a gaseous carrier, a bait or the like, or impregnated into a base material such as porous ceramic plates, non-woven fabrics, etc., and if necessary a surface active agent and other auxiliaries for formulation are additionally added. These formulations contain the present compound as an active ingredient in an amount of usually 0.01 to 95% by weight.

The solid carrier used in the formulation includes for example fine powders or granules of clays (e.g. kaolin clay, diatomaceous earth, synthetic hydrated silicon dioxide, bentonite, Fubasami clay and terra alba), talcs, ceramics, other inorganic minerals (e.g. sericite, quartz, sulfur, activated carbon, calcium carbonate and hydrated silica) and the like. The liquid carrier includes for example water, alcohols (e.g. methanol and ethanol), ketones (e.g. acetone and methyl ethyl ketone), aromatic hydrocarbons (e.g. benzene, toluene, xylene, ethylbenzene and methylnaphthalene), aliphatic hydrocarbons (e.g. hexane, cyclohexane, kerosene and gas oil), esters (e.g. ethyl acetate and butyl acetate), nitriles (e.g. acetonitrile and isobutyronitrile), ethers (e.g. diisopropyl ether and dioxane), acid amides (e.g. N,N-dimethylformamide and N,N-dimethylacetamide), halogenated hydrocarbons (e.g. dichloromethane, trichloroethane and carbon tetrachloride), dimethyl sulfoxide, vegetable oils (e.g. soybean oil and cotton seed oil) and the like. The gaseous carrier, i.e. a propellant, includes for example freon gas, butane gas, LPG (liquefied petroleum gas), dimethyl ether, carbon dioxide gas and the like.

The surface active agent includes for example salts of alkyl sulfate, salts of alkylsulfonate, salts of alkylarylsulfonate, alkyl aryl ethers and their polyoxyethylenized products, polyethylene glycol ethers, polyhydric alcohol esters, sugar alcohol derivatives and the like.

The auxiliaries for formulation such as fixing agents, dispersing agents, etc. include for example casein, gelatin, polysaccharides (e.g. starch powder, gum arabic, cellulose derivatives and alginic acid), lignin derivatives, bentonite, sugars, water-soluble synthetic polymers (e.g. polyvinyl alcohol, polyvinyl pyrrolidone and polyacrylic acids) and the like. The stabilizing agents include for example PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters and the like.

The base material for the poison bait includes for example bait components (e.g. grain powders, vegetable oils, sugars and crystalline cellulose), antioxidants (e.g. dibutylhydroxytoluene and nordihydroguaiaretic acid), preservatives (e.g. dehydroacetic acid), preventives for eating by mistake (e.g. red pepper powder), attracting perfumes (e.g. cheese perfume and onion perfume) and the like.

The preparations thus obtained are used as they are or diluted with water or the like. Also, they may be used in mixture with other acaricidally active compounds, insecticidally active compounds (e.g. tetramethrin and d-allethrin), insecticidally and acaricidally active compounds (e.g. d-phenothrin), microbiocides, synergists, feeds for animals and the like. Alternatively, they may be used separately and yet simultaneously without being mixed together.

The emulsifiable concentrates, wettable powders, flowable concentrates, etc. containing the present compound as an active ingredient are usually applied after diluted with water to a concentration of from 0.1 ppm to 500 ppm. The oil sprays, granules, dusts, fumigants, smoking formulations, aerosols, foggings, poison baits, mite-controlling sheets, etc. containing the present compound as an active ingredient are usually applied as they are.

Both the dosage rate and the concentration of the active ingredient of these formulations vary depending upon the kind of the formulations, when, where and how these formulations are applied, the kind of mites, the degree of damage by mites, etc., and may be increased or decreased irrespective of the ranges mentioned above.

The present invention will be illustrated in more detail with reference to the following production examples, formulation examples and test examples, but it should not be interpreted as being limited to these examples.

First, production examples for the present compounds will be shown.

Production Example 1

Production of compound (1) by Method A 65.7 Grams of 6-phenylhexanoyl chloride was added by drops to a mixture of 19.2 g of propargyl alcohol, 34.7 g of triethylamine and 500 ml of dry toluene with stirring and ice-cooling. After dropwise addition, the resultant solution was stirred for additional 12 hours at room temperature. The thus stirred solution was poured into ice water. The toluene layer was separated from the resulting mixture. The aqueous layer was extracted once with toluene. These toluene layers were combined, washed with water and then with an aqueous saturated sodium chloride solution, and dried over anhydrous magnesium sulfate. The solvent was distilled off from the dried layer under reduced pressure. The resulting residue was distilled under reduced pressure to obtain 157.9 g of propargyl 6-phenylhexanoate.

Yield: 81%
b.p.: 125°–130° C./0.2 mmHg
$n_D^{22.0}$: 1.5031

Production Example 2

Production of compound (2) by Method A

544 Milligrams of 7-phenylheptanoyl chloride was added by drops to a mixture of 135 mg of propargyl alcohol, 191 mg of pyridine and 20 ml of dry toluene with stirring and ice-cooling. After dropwise addition, the resultant solution was stirred for additional 12 hours at room temperature. The thus stirred solution was poured into a dilute hydrochloric acid cooled with ice. The toluene layer was separated from the resulting mixture. The aqueous layer was extracted once with toluene. These toluene layers were combined, washed with water and then with an aqueous saturated sodium chloride solution, and dried over anhydrous magnesium sulfate. The solvent was distilled off from the dried layer under reduced pressure. The resulting residue was subjected to chromatography on silica gel to obtain 482 mg of propargyl 7-phenylheptanoate.

Yield: 81%
$n_D^{27.6}$: 1.4995

Production Example 3

Production of compound (3) by Method A

542 Milligrams of 8-phenyloctanoyl chloride was added by drops to a mixture of 140 mg of propargyl alcohol, 198 mg of pyridine and 20 ml of dry toluene with stirring and ice-cooling. After dropwise addition, the resultant solution was stirred for additional 12 hours at room temperature. The thus stirred solution was then poured into ice water. The toluene layer was separated from the resulting mixture. The aqueous layer was extracted once with toluene. These toluene layers were combined, washed with water and then with an aqueous saturated sodium chloride solution, and dried over anhydrous magnesium sulfate. The solvent was distilled off from the dried layer under reduced pressure. The resulting residue was subjected to chromatography on silica gel to obtain 530 mg of propargyl 8-phenyloctanoate.

Yield: 90%
$n_D^{25.7}$: 1.4972

Production Example 4

Production of compound. (1) by Method B

A mixture of 1 g of 6-phenylhexanoic acid, 292 mg of propargyl alcohol, 5 ml of the monohydrate of p-toluenesulfonic acid and 30 ml of benzene is heated under reflux with stirring while removing formed water by a molecular sieve 4A. After 12 hours, the reaction solution is concentrated under reduced pressure and then subjected to chromatography on silica gel to obtain propargyl 6-phenylhexanoate.

Production Example 5

Production of compound (1) by Method B

Five hundred milligrams of 1-ethyl-3-(3-dimethylaminopropyl)carbodiimide hydrochloride was added to a mixture of 500 mg of 6-phenylhexanoic acid and 20 ml of dry chloroform at room temperature with stirring. After the resultant mixture had been stirred for 30 minutes at room temperature, 146 mg of propargyl alcohol was added thereto at room temperature. Thereafter, the resulting mixture was stirred for 12 hours at room temperature, poured into ice water and extracted with chloroform. The chloroform extract was washed with an aqueous saturated ammonium chloride solution and then with an aqueous saturated sodium chloride solution, dried over anhydrous magnesium sulfate and concentrated under reduced pressure. The resulting residue was subjected to chromatography on silica gel to obtain 155 mg of propargyl 6-phenylhexanoate.
Yield: 26%

Production Example 6

Production of compound (1) by Method C

Two milliliters of a dry N,N-dimethylformamide solution of 618 mg of propargyl bromide is added by drops to a mixture of 1 g of 6-phenylhexanoic acid, 862 mg of potassium carbonate and 20 ml of dry N,N-dimethylformamide at room temperature with stirring. After stirring for 24 hours, the resultant solution is poured into an aqueous saturated ammonium chloride solution cooled with ice. The resulting mixture is then extracted twice with diethyl ether. The extracts are combined, washed with water and then with an aqueous saturated sodium chloride solution, dried over anhydrous magnesium sulfate and concentrated under reduced pressure. The resulting residue is subjected to chromatography on silica gel to obtain propargyl 6-phenylhexanoate.

Some of the present compounds thus produced are shown in Table 2.

TABLE 2

| Compound number | Compounds of the formula (I) | | Physical property |
|---|---|---|---|
| | $(R^1)_m$ | Z | |
| 1 | H | $-(CH_2)_5-$ | $n_D^{22.0}$ 1.5031 |
| 2 | H | $-(CH_2)_6-$ | $n_D^{27.6}$ 1.4995 |
| 3 | H | $-(CH_2)_7-$ | $n_D^{26.7}$ 1.4972 |
| 4 | H | $-(CH_2)_8-$ | $n_D^{26.2}$ 1.4969 |
| 5 | H | $-(CH_2)_9-$ | $n_D^{25.1}$ 1.4950 |
| 6 | H | $-(CH_2)_{10}-$ | $n_D^{24.6}$ 1.4936 |
| 7 | H | $-(CH_2)_3-CH-CH_2-$ $\quad\quad\quad\quad\;\;\;\vert$ $\quad\quad\quad\quad\;\;\;CH_3$ | $n_D^{23.7}$ 1.5016 |

Formulation examples are shown. In the examples, all parts are by weight, and the present compounds are indicated by the compound numbers in Table 2.

Formulation Example 1

Emulsifiable Concentrate

Ten parts of each of the compounds (1) to (7) is dissolved in a mixture of 35 parts of xylene and 35 parts of dimethylformamide. To the resultant mixture are added 14 parts of polyoxyethylene styrylphenyl ether and 6 parts of calcium dodecylbenzenesulfonate. The resulting mixture is thoroughly stirred and mixed to obtain an emulsifiable concentrate containing each of the compounds (1) to (7) in a concentration of 10%.

Formulation Example 2

Wettable Powder

Twenty parts of each of the compounds (1) to (7) is added to a mixture of 4 parts of sodium lauryl sulfate, 2 parts of calcium lignosulfonate, 20 parts of the fine powder of synthetic hydrated silicon dioxide and 54 parts of diatomaceous earth. The resulting mixture is stirred and mixed by a juice mixer to obtain a wettable powder containing each of the compounds (1) to (7) in a concentration of 20%.

Formulation Example 3

Dust

One part of each of the compounds (1) to (7) is dissolved in a suitable amount of acetone. To the resulting solution are added 5 parts of the fine powder of synthetic hydrated silicon dioxide, 0.3 part of PAP and 93.7 parts of clay. The resulting mixture is stirred and mixed by a juice mixer. Then, acetone is removed from the thus stirred mixture by evaporation to obtain a dust containing each of the compounds (1) to (7) in a concentration of 1%.

Formulation Example 4

Flowable Concentrate

Twenty parts of each of the compounds (1) to (7) and 1.5 parts of sorbitan trioleate are mixed with 28.5 parts of an aqueous solution containing 2 parts of polyvinyl alcohol. The resulting mixture is finely pulverized, if necessary, to a particle size of 3μ or less with a sand grinder. To the mixture are added 40 parts of an aqueous solution containing 0.05 part of xanthane gum and 0.1 part of aluminum magnesium silicate and then further 10 parts of propylene glycol. The resulting mixture is stirred and mixed to obtain a water-based suspension formulation containing each of the compounds (1) to (7) in a concentration of 20%.

Formulation Example 5

Oil Spray 0.1 Part of each of the compounds (1) to (7) is dissolved in a mixture of 5 parts of xylene and 5 parts of trichloroethane. The resulting solution is mixed with 89.9 parts of deodorized kerosene to obtain an oil spray containing each of the compounds (1) to (7) in a concentration of 0.1%.

Formulation Example 6

Oil-based Aerosol 0.1 Part of each of the compounds (1) to (7), 0.1 part of d-phenothrin, 10 parts of trichloroethane and 59.8 parts of deodorized kerosene are mixed into a solution. The resulting solution is put in an aerosol container.

Then, a valve portion is attached to the container. Thereafter, 30 parts of a propellant (liquefied petroleum gas) is compressed into the container through the valve portion to obtain an oil-based aerosol containing each of the compounds (1) to (7).

Formulation Example 7

Oil-based Aerosol 0.1 Part of each of the compounds (1) to (7), 0.2 part of tetramethrin, 0.1 part of d-phenothrin, 10 parts of trichloroethane and 59.6 parts of deodorized kerosene are mixed into a solution. The resulting solution is put in an aerosol container. Then, a valve portion is attached to the container. Thereafter, 30 parts of a propellant (liquefied petroleum gas) is compressed into the container through the valve portion to obtain an oil-based aerosol containing each of the compounds (1) to (7).

Formulation Example 8

Oil-based Aerosol

One part of each of the compounds (1) to (7), 7 parts of kerosene and 32 parts of deodorized kerosene are mixed into a solution. The resulting solution is put in an aerosol container. Then,, a valve portion is attached to the container. Thereafter, 60 parts of a propellant (liquefied petroleum gas) is compressed into the container through the valve portion to obtain an oil-based aerosol containing each of the compounds (1) to (7).

Formulation Example 9

Water-based Aerosol 0.2 Part of each of the compounds (1) to (7), 0.2 part of d-phenothrin, 5 parts of xylene, 3.6 parts of deodorized kerosene and 1 part of an emulsifier (Atmos 300, a registered trade mark of Atlas Chemical Co., Ltd.) are mixed into a solution. The resulting solution and 50 parts of pure water are put in an aerosol container. Then, a valve portion is attached to the container. Thereafter, 40 parts of a propellant (liquefied petroleum gas) is compressed into the container through the valve portion to obtain a water-based aerosol containing each of the compounds (1) to (7).

Formulation Example 10

Water-based Aerosol 0.2 Part of each of the compounds (1) to (7), 0.2 part of d-allethrin, 0.2 part of d-phenothrin, 5 parts of xylene, 3.4 parts of deodorized kerosene and 1 part of an emulsifier (Atmos 300, a registered trade mark of Atlas Chemical Co., Ltd.) are mixed into a solution. The resulting solution and 50 parts of pure water are put in an aerosol container. Then, a valve portion is attached to the container. Thereafter, 40 parts of a propellant (liquefied petroleum gas) is compressed into the container through the valve portion to obtain a water-based aerosol containing each of the compounds (1) to (7).

Formulation Example 11

Heating Smoking Formulation

One hundred milligrams of each of the compounds (1) to (7) is dissolved in a suitable amount of acetone. A porous ceramic plate (length: 4.0 cm, width: 4.0 cm, thickness: 1.2 cm) is impregnated with the solution to obtain a heating smoking formulation containing each of the compounds (1) to (7).

Formulation Example 12

Poisonous Bait

Ten milligrams of each of the compounds (1) to (7) is dissolved in 0.5 ml of acetone. The resulting solution and 5 g of a solid feed powder for animals (CE-2, a solid feed powder for breeding; a trade name of Clea Japan, Inc.) are mixed together uniformly. Thereafter, acetone is removed by air-drying to obtain a poisonous bait containing each of the compounds (1) to (7) in a concentration of 0.2%.

Formulation Example 13

Mite-controlling Sheet

Each of the compounds (1) to (7) is diluted with acetone. The resulting solution is dropped to a nonwoven fabric and is allowed to soak into the fabric so that the fabric contains each of the compounds (1) to (7) in an amount of 1 g per square meter of the fabric. Thereafter, acetone is removed from the fabric by air-drying to obtain a mite-controlling sheet containing each of the compounds (1) to (7).

Formulation Example 14

Mite-controlling Sheet

Each of the compounds (1) to (7) is diluted with acetone, and the resulting solution is dropped to a filter paper and is allowed to soak into the paper so that the paper contains each of the compounds (1) to (7) in an amount of 1 g per square meter of the paper. Thereafter, acetone is removed from the paper by air-drying to obtain a mite-controlling sheet containing each of the compounds (1) to (7).

The usefulness of the present compounds as an active ingredient for acaricides will be illustrated with reference to the following test examples. In the examples, the present compounds are indicated by the compound numbers in Table 2. The following compound of the formula (I), wherein Z represents an ethylene group and $(R_1)_m$ represents a hydrogen atom, was used as a comparative compound.

Compound A: propargyl 3-phenylpropionate

Test Example 1

A filter paper of 4 cm in diameter was uniformly treated with an acetone solution of the test compound so that the filter paper contained the compound in an amount of 0.8 g/m$^2$ of the filter paper. The thus treated filter paper was air-dried. An adhesive substance was coated on the edge of the filter paper in order to prevent the mites from running away. About 20 heads of each of common grain mite (*Tyrophagus putrescentiae*), *Dermatophagoides farinae* Hughes and *Dermatophagoides pteronyssinus* were freed on the surface of the filter paper. After one day, the mites were examined for mortality.

Tables 3, 4 and 5 show the results obtained on *Tyrophagus putrescentiae*, *Dermatophagoides farinae* Hughes and *Dermatophagoides pteronyssinus*, respectively.

TABLE 3

| Activity against *Tyrophagus putrescentiae* | |
|---|---|
| Compound | Mortality (%) |
| (1) | 100 |
| (2) | 100 |
| (3) | 100 |
| (4) | 100 |

TABLE 3-continued

Activity against *Tyrophagus putrescentiae*

| Compound | Mortality (%) |
|---|---|
| (5) | 100 |
| (6) | 100 |
| (7) | 100 |
| No treatment | 0 |

TABLE 4

Activity against *Dermatophagoides farinas* Hughes

| Compound | Mortality (%) |
|---|---|
| (1) | 100 |
| (2) | 100 |
| (3) | 100 |
| (4) | 100 |
| (7) | 100 |
| No treatment | 0 |

TABLE 5

Activity against *Dermatophagoides pteronyssinus*

| Compound | Mortality (%) |
|---|---|
| (1) | 100 |
| (2) | 100 |
| (3) | 100 |
| (4) | 100 |
| (5) | 94 |
| (7) | 100 |
| No treatment | 0 |

Test Example 2

A filter paper of 4 cm in diameter was uniformly treated with an acetone solution of the test compound so that the filter paper contained the compound in an amount of 0.8 g/m² of the filter paper. The thus treated filter paper was air-dried. An adhesive substance was coated on the edge of the filter paper in order to prevent the mites from running away. Seven days after treatment, about 20 heads of *Dermatophagoides pteronyssinus* was freed on the surface of the filter paper. One day later (at the 8th day after treatment), the mites were examined for mortality. Table 6 shows the results.

TABLE 6

| Compound | Mortality (%) |
|---|---|
| (1) | 93 |
| (2) | 98 |
| (3) | 98 |
| (A) | 17 |
| No treatment | 0 |

Thus, it is demonstrated that the present compounds have an excellent acaricidal activity.

What is claimed is:

1. A propargyl ester compound of the formula (I),

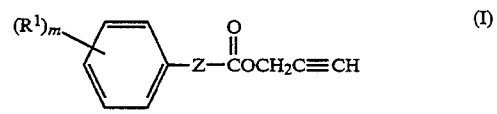

wherein $R^1$ is hydrogen, halogen, $C_1$-$C_4$ alkyl or $C_1$-$C_4$ alkoxy; Z is $C_5$-$C_{10}$ alkylene which may be substituted with $C_1$-$C_4$ alkyl; and m is an integer of from 1 to 5; with the proviso that when m is an integer of from 2 to 5, the substituents represented by $R^1$ may be the same or different.

2. A propargyl ester compound according to claim 1, wherein $R^1$ and m in the formula (I) are selected so that:
when m is 1, $R^1$ is hydrogen, fluorine, chlorine, $C_1$-$C_4$ alkyl or $C_1$-$C_4$ alkoxy;
when m is 2, one of the substituents represented by $R^1$ is hydrogen, fluorine, chlorine, $C_1$-$C_4$ alkyl or $C_1$-$C_4$ alkoxy, and the other substituent represented by $R^1$ is hydrogen, fluorine, chlorine or methyl,
when m is an integer of from 3 to 5, one of the substituents represented by $R^1$ is hydrogen, fluorine, chlorine, $C_1$-$C_4$ alkyl or $C_1$-$C_4$ alkoxy, and the other substituents represented by $R^1$ are independently hydrogen, fluorine, chlorine or methyl.

3. A propargyl ester compound according to claim 1, wherein m is an integer of from 1 to 2.

4. A propargyl ester compound according to claim 1, wherein the molecular weight of the propargyl ester compound falls within the approximate range of from 230 to 300.

5. A propargyl ester compound of the formula,

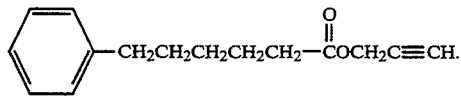

6. An acaricidal composition which comprises an acaricidally effective amount of a propargyl ester compound according to claim 1 as an active ingredient and an inert carrier.

7. A method for controlling acarines which comprises applying an acaricidal composition according to claim 6 to a locus where the acarines inhabit.

8. A method for controlling acarines according to claim 7, wherein the acarines are house dust mites.

* * * * *